United States Patent [19]

Blanchette et al.

[11] Patent Number: 5,472,874
[45] Date of Patent: Dec. 5, 1995

[54] PITCH DEGRADATION WITH WHITE ROT FUNGUS

[75] Inventors: Robert A. Blanchette, Shoreview, Minn.; Roberta L. Farrell, Groton; Sara Iverson, Lexington, both of Mass.

[73] Assignee: Sandoz Ltd., Basel, Switzerland

[21] Appl. No.: 247,130

[22] Filed: May 20, 1994

[51] Int. Cl.⁶ .............................. D21C 9/08; D21C 3/00; D21C 5/00; C12P 1/02
[52] U.S. Cl. ................. 435/278; 162/9; 162/72; 435/171; 435/254.1; 435/267; 435/277; 435/911
[58] Field of Search .................. 435/171, 254.1, 435/911, 277, 267, 278, 911; 162/9, 72

[56] References Cited

U.S. PATENT DOCUMENTS 3,486,969  12/1969  Nilsson et al. .......................... 162/72
5,055,159  10/1991  Blanchette et al. ..................... 162/72

FOREIGN PATENT DOCUMENTS 387187  9/1990  European Pat. Off. .
470929  2/1992  European Pat. Off. .

OTHER PUBLICATIONS

Chem Abs: 117(6) 51099f Perrolaz et al "Rev ATIP" 46(1) pp. 12–16 (1992).

Chem Abs: 92 (320935) CA Previews ABS of BR9001398 (Nov. 5, 1991).

Chem ABS 118(4) 23144e Wendler et al "Kem–Kemi" 19(3) 262-4 (1992).

Primary Examiner—Herbert J. Lilling
Attorney, Agent, or Firm—Robert S. Honor; Carl W. Battle; Michael P. Morris

[57] ABSTRACT

The fungus *Phlebia tremellosa* is useful in reducing the pitch content of pulps and pulpwoods used in making cellulosic products.

18 Claims, No Drawings

PITCH DEGRADATION WITH WHITE ROT FUNGUS

The present invention relates to the use of certain fungi in the reduction of the pitch content of materials used in the manufacture of cellulosic products.

Wood is a complex material composed of cellulose, hemicellulose, lignin and wood extractives or a resinous material commonly called "pitch", "resin" or "wood resin". The composition of pitch has been studied and is reported widely in the literature, e.g., *Wood Extractives and Their Significance to the Pulp and Paper Industry,* Chapter 10 "Wood Resins" by D. B. Mutton; W. E. Hillis, Ed, Academic Press, New York (1962).

In the production of products from wood pulps, the presence of pitch is undesirable as due to its viscosity and tenacity it frequently forms deposits which are difficult to remove, causing relatively frequent and lengthy periods of down-time for cleaning, as resins tend to accumulate as deposits on strainer plates, filters, and throughout paper processing apparatus. It is well-known that pitch may also discolor pulp and paper formed therefrom if allowed to accumulate too long before cleaning. Other drawbacks are known in the art, e.g. waste stream pollution.

In Nilsson, et al., U.S. Pat. No. 3,486,969, it is disclosed that certain fungi may be used to inoculate wood chips to reduce the resin content therein and the pulp therefrom while minimizing degradation of the other components of the wood, especially cellulose and hemicellulose. The species of fungi therein disclosed however, are apparently all mold type or surface forming fungi which, when discoloring the wood, produce essentially a surface or superficial stain which may be readily planed off (see J. S. Boyce, *Forest Pathology,* 3rd. Ed., 1961, McGraw-Hill Book Co. at pp. 493–512, especially 496–497). Such fungi have failed to achieve practical success to our knowledge.

In published European patent application EP 03 87 187 A2 (based on U.S. patent application Ser. No. 310,814, filed 13 Feb. 1989) there are described the application of certain wood-penetrating fungi generally classed as Ascomycetes or Deuteromycetes to pulpwoods and pulps to reduce the pitch content thereof. Similarly useful wood-penetrating fungal derivatives are also disclosed in published European patent application EP 04 70 929 A2 (based on U.S. patent applications having Ser. No. 560,521, filed Jul. 31, 1990 and copending Ser. No. 657,581, filed Feb. 19, 1991).

In copending U.S. patent application Ser. No. 889,796, filed Jun. 17, 1992, there are described other strain derivatives of a preferred wood-penetrating fungus *Ophiostoma piliferum* which exhibit very good pitch degrading and aggressive growth characteristics while growing white or colorless on treated substrates.

A succession of preferred and improved wood-penetrating strains of *O. piliferum* as above-described have demonstrated commercial capability and have achieved commercial success. In addition to substantial savings from pitch reduction, early indications of greater paper strength (translating into faster machine speeds) have been confirmed and there are further indications of greater pulping efficiency, particularly for example when used on substrates for chemical pulping, probably due to the ability of the fungus to substantially open up resin ducts and ray parenchyma cells. The ability of such fungi to be useful practically is in part attributed to the ability of the fungi to grow competitively on non-sterile substrates and not be excluded or dominated by other fungi or organisms which naturally infect wood sources. In retrospect, one can at least theorize why the indicated wood-penetrating fungi are able to be useful and provide the indicated advantages. For example, the indicated wood-penetrating fungi are known to be early colonizers of dead wood and hence early contributors to the process of wood decay. One might therefore imagine that a major natural purpose of such fungi is the substantial removal or reduction of resin in the wood, a process which would also open up the resin ducts and parenchyma cells to the invasion of the later colonizing rotting fungi, such as the white rots and brown rots which are, for example, commonly found in the fungal classification Basidiomytes (Basidiomycotina). The ability of the indicated wood-penetrating fungi to dominate other fungi including Basidiomytes when substantial resin is present perhaps ensures that their pitch-degrading purpose is served and would be consistent with the theory that their primary natural purpose may be pitch degradation.

In the general field of research of the potential use of fungi and fungal enzymes in paper making, the Basidiomytes, particularly white rot fungi, have been of interest for their ability to degrade lignin and produce lignin degrading enzymes. The original concept referred to as "biopulping" was founded on the idea of an early treatment of pulpwood, e.g. in the form of wood chips, to begin the process of pulping or lignin removal prior to entry into the pulp mill itself. A white rot fungi judged particularly suitable for such purpose is *Ceriporiopsis subvermispora* as described in U.S. Pat. No. 5,055,159. While the cause or mechanism of action of such fungus in obtaining its desirable effects are indicated in the patent to be related to selective lignin degradation, we have noted that some reported benefits are also suggestive of those obtained by our above-indicated pitch degrading fungi. Consistent with our general understanding concerning Basidiomycetes, the fungus *Ceriporiopsis subvermispora* does not grow well on non-sterile substrates and the subject patent discloses the sterilization of the substrates prior to inoculation with the fungus.

An objective of the present invention is to expand the field of fungi useful in degrading pitch in pulps and pulpwoods, and particularly in non-sterile substrates.

Another object is to provide pitch degrading fungi having or combining desired properties such as color effects, pitch-degrading ability, good growth on non-sterile substrates, flexibility in temperature of operation, greater action or flexibility of action on different wood species and the like.

In accord with the present invention, it has been found that white rot fungus, *Phlebia tremellosa,* is desirably effective in reducing the pitch content of wood substrates, including particularly pitch in non-sterilized wood substrates.

Accordingly, the invention provides a method of reducing the pitch content of wood, particularly pulpwoods and pulps, said method comprising applying to pulpwood or pulp an inoculum of the fungus species *Phlebia tremellosa,* and thereafter maintaining the inoculated pulpwood or pulp under conditions allowing growth of the fungus for a time sufficient to reduce the pitch content of the pulpwood or pulp.

By the terms "resin" or "pitch" (which are used interchangeably) is meant that complex mixture of hydrophobic substances in wood, commonly known as pitch, which are soluble in neutral organic solvents, such as methylene chloride, diethyl ether, benzyl alcohol and the like. These include the terpenes, the diterpene ("resin") acids, fatty acids and esters, glycerides and waxes as well as alcohols, hydrocarbons and other compounds associated therewith. For purposes of this invention, the standard Tappi extraction analysis using methylene chloride will suffice for measuring the reduction in resins which is the object of the invention.

However, other recognized solvent systems such as ethanol/toluene are essentially equally representative.

Resin or pitch is a significant constituent of both softwood, such as southern pine, conifers and cedars, and hardwoods, such as Betula and Populus, and it may comprise as much as 4% weight percent or even more of the feed sent to mechanical or chemical pulping processes, generally 1.5 to 4.0% for most woods used for pulping. Softwoods generally contain more resin than hardwoods, with pines having among the highest resin content among softwoods. In hardwoods, resin is located primarily in the ray parenchyma cells which form much of the fiber fraction when wood is pulped. In softwoods, resin is contained in both the ray parenchyma cells and also in resin ducts.

The invention may be generally applied to reduce the pitch content of pulpwoods and pulps used in the manufacture of cellulosic products.

The term "pulpwood" as used herein means any harvested (cut down) form of a tree material used in making paper, cardboard or other cellulosic products such as viscose, but prior to pulping, and includes such forms as timber, logs, wood chips, sawdust and the like. The term "refined pulpwood" means a pulpwood resulting from the application of mechanical and/or shearing forces to whole pulpwood forms such as logs to obtain a multiplicity of high surface area, small pieces, such as wood chips and sawdust, which are introducible into a pulping process. The invention may also be applied to lignin-containing cellulosic materials classifiable as pulps which have yet to undergo sufficient treatment to significantly reduce its lignin content (and liberate contained pitch), in particular pulp which still retains 60% or more of its original lignin content, such as first stage mechanical pulp. The invention may therefore be utilized in one aspect thereof to at least partially reduce the resin component of refined pulpwood and incompletely refined pulps by applying to the pulpwood or pulp an inoculum of at least one of the indicated fungi, accumulating the inoculated pulpwood or pulp in a mass and maintaining the accumulated mass under conditions which allow or promote fungal growth in the mass for a time sufficient to effect a reduction in the resin component of the pulpwood or pulp by the fungus. The invention may be applied to unrefined pulpwoods such as cut timber in debark or undebarked form by inoculating the timber, desirably at least partially scored in the case of undebarked timber, and maintaining the timber for a time sufficient to allow growth of the fungus on and into the wood substrate and effect a reduction in the resin component thereof.

By the term "inoculum" and the like as used herein is meant any fungal material which is sufficiently viable to result in growth of the fungus when applied to the substrate. Typical fungal inoculums include fungal cultures or preparation obtained from a fungal culture, desirably from a biologically pure culture. The basic structural unit of most fungi in the fungal filament or "hypha". In aggregate, these filaments comprise a fungal body call "mycelium". Fungi typically reproduce asexually by means of spores called conidia which are given off by the mycelia, have resting structures called chlamydiospores or may reproduce sexually by means of basidiospores. All such forms and fungal elements, e.g. mycelia and spores, may be suitably used as inoculum in the invention. An inoculum form may be provided by culturing the fungus in any of several conventional ways. Solid or liquid culturing media may be used as desired or required, preferably liquid media. Culturing of the fungus under conditions favoring spore formation is usually preferred when possible, and the generally preferred inoculum will contain a large number of spores resulting from the fungal culture.

The inoculum may be in solid or liquid form. Whole liquid cultures or portions thereof may be used, e.g. mixtures of mycelia and spores. When a high content of spores is available in the culture, the product may be lyophilized (freeze-dried) to obtain a dry inoculum in which spores constitute the viable component to generate the fungus after inoculation. Inocula in the form of concentrates to be diluted with water for application are generally stored at temperatures which will preserve desired viability. Liquid forms are usually stored frozen, typically at temperatures of from $-5°$ C., to $-80°$ C., more usually $-10°$ C. to $-75°$ C. Dry forms are similarly stored although lyophilized forms containing spores as the operable inoculum are often more stable and may be stored at higher temperatures than counterpart liquid forms. Inoculum compositions may comprise other ingredients such as preservatives and stabilizing agents or inert carriers introduced in certain types of drying processes.

The inoculum may be applied to the wood substrate in a variety of manners. Typically, the inoculum is applied in a systematic or methodical manner. For example, the inoculum is distributed at intervals in the mass of refined pulpwood, or on the outer surface of a cut timber, preferably at regular intervals. More preferably, the inoculum is distributed in a homogeneous or uniform manner, i.e. substantially throughout the mass of refined pulpwood. However, it is not necessary that each individual wood chip, sawdust particle and the like be inoculated. As little as 10% or even less but preferably about at least 20%, more preferably at least about 50%, of the individual pieces can be inoculated since the uninoculated pieces are accumulated in contact with the inoculated pieces. Upon growth, the infection will spread very easily.

A thorough or uniform inoculation of a mass of wood chips is generally reflected by the fact that the fungus grows substantially throughout the mass. However, it may happen that some part of the mass, particularly the outer layer of a pile of refined wood pulp, will show little growth compared to the rest of the mass, or no growth at all, although it has been inoculated.

In one preferred embodiment, the inoculum is sprayed onto wood chips or sawdust as they are discharged from the refining operation but before being accumulated into piles. For example, a wood chipping apparatus is generally provided with conveyor means which receive the newly prepared chips and convey them to the accumulating pile. A spray applicator containing the inoculum preparation may be conveniently adapted to the conveyor, preferably at the junction with the chipper when the chips are airborne e.g. free falling or tumbling, or at the very end of the conveyor so that chips are sprayed just before falling from the conveyor.

Alternatively, the inoculum may be applied to the wood chip pile in the course of its accumulation by more or less continuous spraying over the accumulating pile.

When treating pulps or refined pulpwood, the dosage applied may vary depending upon several factors such as the wood being treated, condition or age of the wood, growth conditions, desired treatment time and the like. In general, satisfactory results can be obtained upon application of an inoculation containing from 0.5 to 10 grams of mycelia (wet weight of dewatered mycelia, see Example 1) per 100 grams of pulp or pulpwood, preferably from 1 to 5 grams of mycelia per 100 grams of substrate to be treated. Such mycelia prior to dewatering may be prepared as described in Example 1 or Example A, below, preferably Example A, and may contain spores. Dosage of an inoculation based predominantly or solely on spores may be routinely determined and can be indicated to range from $10^5$ to $10^{10}$ CFU (colony forming units) per kilogram of substrate, more usually from $10^6$ to $10^9$ CFU per Kg. Similarly, expressed dosages of mycelia may be determined and applied. For example, mycelia may be homogenized, e.g. 5–10 minutes, and the number of colonies formed from the fragments when grown on a nutrient medium may be approximated in a conventional manner to determine CFUs for a given volume. The inoculum dosage will generally be applied in a water-diluted sprayable composition, for example, a composition to be applied in a volume of from 20 to 60 ml. per Kg. of substrate. The fungus is preferably applied to freshly cut or refined pulpwood or freshly cut substrates frozen or stored at reduced temperatures until treatment, or the substrate sterilized. When applied to non-sterile pulpwood which has been allowed to age before treatment, e.g. wood chips which were produced about 5 days or more before treatment, it may be desirable to increase the inoculum dosage to the higher end of the dosage range in order to avoid, suppress or overcome the background growth effects of fungi which naturally infected the wood prior to inoculation.

In another embodiment, chips which have been previously inoculated and incubated according to the invention may be dispersed into fresh chips to effect or enhance inoculation. Such an inoculum is likely to be not biologically pure. However, it reflects the previous inoculation as at least 40%, preferably at least 50% of the inoculum is the desired fungus.

After inoculation, the accumulated mass is maintained under conditions which will allow or promote the growth of the fungus substantially throughout the mass. Given the fact that the invention will in most cases be likely to be practiced in open air and the mass therefore subjected to a wide variety of weather conditions, the maintenance of any given set of ideal conditions throughout the entire treatment period is usually too difficult to achieve and is often unnecessary in practice. It is generally sufficient that the mass be substantially maintained at a temperature at which the fungus grows while avoiding higher temperatures at which the fungus dies. While our fungus may exhibit some reasonable growth at or below 0° C. it will generally be more suitable to have a temperature of at least 10° C. such as a temperature of from 10° C. to 45° C. more preferably of from 15° C. to 40° C., most preferably of from 22° C. to 36° C.

In mild or warm weather conditions, it is not necessary to influence the environmental temperature and the inoculated mass may be left to stand in open air without special maintenance. In cold weather conditions, it may be desirable to provide the inoculated mass with means for maintaining the more suitable temperatures. This may be a heat-retaining covering placed over or on the inoculated mass such as a large plastic sheet. Alternatively, the ground base on which is placed the inoculated mass may be provided with heating pipes or a plurality of openings for releasing warm air or steam. In a similar manner, a concrete "igloo" or similar structure which can be internally heated and emit radiant heat may be used to support the accumulated mass of pulpwood. When providing heating means, it would also be desirable to control the moisture conditions to avoid an excessive dryness. In view of this, means for venting the heat or steam would be adequate. However, due to the heat generated in an accumulated mass from fungal growth and other microbial or natural effects, operation under many cold weather conditions may proceed satisfactorily with little or no assistance.

The period of time during which the inoculated refined pulpwood mass is treated may vary considerably depending upon a number of factors including the desired extent of resin removal, the temperature and moisture conditions, the extent of inoculation and the like. However, satisfactory results may generally be obtained after a period of time extending from 3 to 40 days, preferably from 4 to 30 days. Under preferred conditions, very effective results e.g. a pitch reduction of about 20% or more, may be obtained 4 to 20 days after the inoculation, more usually 5 to 15 days.

Treatment of unrefined pulpwood, such as cut timbers, will usually be somewhat longer than that of refined pulpwood and may extend up to 2 months. However, treatment of pulps and pulpwoods with the indicated fungus generally should be conducted for periods which effect desired pitch reduction while avoiding excessive periods which might result in any substantial attack on the cellulose component of the substrate(s). Dosages for unrefined pulpwood may be similar to those for refined pulpwood and applied over from 10% to 100% of available surfaces, more usually over 15% to 50% of the available surfaces.

The fungus used in carrying out the invention is a previously known species and may be obtained in a known manner, e.g. by isolation from wood sources on which they grow in nature. While some variation among strains can be expected depending on factors such as the wood source from which they may be isolated, our fungus demonstrated remarkable growth on both unsterilized Southern Yellow Pine and also on hardwoods, such as maple and birch, and can be expected to grow well on other wood types commonly used in making cellulosic products. Naturally occurring isolates of our fungus can be modified by various known means of strain selection, mating and mutation without losing their identifying species characteristics. Hence, our preferred natural isolates have been deposited with the Northern Regional Research Center (NRRL), as detailed below, but it will be apparent that the same can be modified and that preferred fungal strains will include not only such isolates but also all other isolates and modifications which substantially possess at least the pitch degrading and/or growth properties on sterilized Southern Yellow Pine that are possessed by either deposited strain. The fungus used in the invention will grow white or essentially colorless on pulpwood and pulp. Since they may be used to largely or completely dominate other darker growing fungus which naturally infect unsterilized substrates, the fungus of the invention may be used to produce a product requiring less bleaching to obtain the final paper product.

DEPOSITS

We have under the Budapest Treaty deposited with the Northern Regional Research Center (NRRL) at Peoria, Ill., U.S.A. a biologically pure specimen of two isolates, which deposits were assigned the Accession Numbers given below along with their date of deposit.

| Fungus | Accession No. | Deposit Date |
| --- | --- | --- |
| *Phlebia tremellosa* BRI-94 | NRRL 21200 | February 17, 1994 |
| *Phlebia tremellosa* BRI-118 | NRRL 21253 | May 16, 1994 |

The strains in the above deposits are identified below as isolate BRI-94 and isolate BRI-118.

The above deposits were obtained as natural isolates from fallen timber in the State of Minnesota, U.S.A., but other isolates can be obtained from a variety of other global locations. The fungus was isolated from hardwood. The classification of our fungus as *Phlebia tremellosa* is in accord with Ainsworth & Bisby's dictionary of the Fungi, 7th Edition, 1983 D. L. Hawksworth, B. C. Sutton, & G. C. Ainsworth, Commonwealth Mycological Institute Kew, Surrey UK.

EXPERIMENTAL

General Procedures: Cultures and Inoculation:

Various evaluations are made on pulpwood substrates to determine pitch reduction and growth. For evaluation of softwood characteristics, sterile and non-sterile Southern Yellow Pine wood chips were used. For evaluation of hardwood characteristics, non-sterile wood chips comprising mainly birch and maple were used. Wood chips are stored at 50° C. prior to evaluation. Each evaluation was performed on substrates of the same wood species and upon wood chips samples which were obtained from the same wood chip source. For each test, individual sample lots of wood chips were first weighed, after which the wood chip samples to be sterilized were heated in an autoclave at 121° C. for about 20 minutes and allowed to cool to room temperature prior to the initiation of a test. The wood chip samples which were to be in non-sterile form were untreated and used in their natural condition. Individual sample lots were prepared by placing measured amounts of wood chips into individual transparent plastic bags; the bags were of sufficient size such that they were closeable (although not hermetically sealable). The use of a transparent bag allowed for the visual inspection of the growth of chips, and to further allow for admission of ambient light to the sample of wood chips being evaluated.

A YNPD liquid culture medium was prepared using the following constituents (amounts are grams per liter of liquid culture medium produced):

10 g glucose 10 g malt extract 2 g peptone 2 g yeast extract 2 g $KH_2PO_4$ 1 g asparagine 1 g $MgSO_4 \cdot 7H_2O$ which are added in sequential order to one liter of distilled water, and subsequently autoclaved at 121° C. for about 20 minutes, and allowed to cool to room temperature. Afterwards, 1 mg. of thiamine is added to the other constituents, after which the YNPD media was ready for use.

Using the YNPD culture media prepared as indicated above, each of the fungi was prepared under the following general conditions:

(a) samples of the particular fungus were used to inoculate sterile petri dishes which contained the YNPD culture media as prepared above, and the dishes were covered;

(b) the inoculated YNPD culture media was maintained at room temperature (approximately 20° C.) until it was visually discernible that the inoculated fungus had grown well upon the YNPD culture media in the form of mycelial mats (about 5 days);

(c) after good growth had been observed, the mycelial mats were then removed in hand (covered with a rubber glove) from the petri dish, the mat squeezed in hand until essentially no further water was emitted and the squeezed mat weighed to determine the "wet weight".

The squeezed or dewatered mat was introduced into a clean laboratory beaker where it was then homogenized with the addition of between 5–10 ml. of distilled water to form a pipetteable slurry which could then be removed from the beaker and used to inoculate a substrate; and (d) the contents of the beaker were then introduced into a graduated cylinder to determine the volume of the pipetteable slurry, and once determined, the contents were returned to the laboratory beaker, from whence they were withdrawn for inoculation of samples.

The inoculation of a sample of wood chips was done by injecting the contents of the pipette containing 2–5 grams wet weight of the mycelial mat for each 100 grams of wood chips, after which the open end of the bag was folded over, and the contents of the bag shaken and tumbled so to maximize the number of chips that came into contact with the inoculant. The folded over end of the bag was stapled at two places. All inoculated wood chip samples were then placed on a laboratory benchtop at room temperature for the periods indicated in each specific test. Each test was performed on two to five samples; reports of the growth of fungi reported herein are the average of these plural results.

Pitch Content Evaluations:

Evaluation of the pitch content of substrates was determined according to standard TAPPI Procedure T204 OM-88 which provides results expressible as milligrams of pitch content per gram of substrate extracted with "DCM" which is methylene chloride. In accordance with the TAPPI Procedure, as used on a substrate such as wood chips, the treated chips are dried overnight at 60° C. and then ground into sawdust using a Thomas-Wiley Mill with 10-mesh screen (10 gauge wire screen). Three grams of the dried sawdust are combined with 30 ml. of DCM and the resulting mixture is agitated overnight (about 15 hours) at room temperature (approximately 20° C.). The liquid medium is pipetted from the mixture, filtered through an organic filter having a pore size of 0.45 μm, and then the liquid is allowed to evaporate at room temperature overnight in a tared (preweighed) dish. The dish residue is then heated in an air-circulation oven at 60° C. for 30 minutes to further remove any residual DCM, after which the dish is allowed to cool to room temperature and reweighed; the weight of the remaining residue, viz., the remaining pitch, is determined and expressed in units of milligrams (mg.) and correlated to the amount of the original sample being evaluated so to provide an expression of mg. of pitch per gram of substrate wood chip, or in the alternative as the percent DCM extractables present in the substrate wood chip sample, which result is equated to and taken as the percent of pitch in the substrate (% extractives). Pitch evaluations may be conducted on both sterile and non-sterile substrates. Evaluations on sterilized substrates will usually eliminate any possible influence of other organisms which naturally infect the substrate. An evaluation on a sterilized substrate can be generally considered the more objective measure of the fungus to reduce pitch on a particular substrate. However, whether conducted on a sterilized or non-sterilized substrate, pitch reduction is generally evaluated relative to an untreated control which is sterilized (for sterilized or substrate tests) held in the frozen state during the test period (non-sterilized substrate evaluation). In general, it is desired to achieve a pitch reduction relative to such a control of at least 20% in no more than 21 days after inoculation, preferably in no more than 14 days. Particularly good results are indicated when pitch is reduced 25% in no more than 21 days, and especially when such reduction is achieved in no more than 14 days. Note that in Example 4, below, a solution of ethanol and toluene (2:1 weight ratio) was used instead of methylene chloride as the extractant.

Growth Evaluations:

Evaluations of the growth of the fungus is made as uniformly as possible and in a manner as nearly identical as possible for all of the individual samples being evaluated for each of the several tests where the growth is to be determined. Evaluation is done using simple visual observation with a protocol applied on a consistent basis and carried out at each evaluation interval (where an intermediate evaluation is performed during a test) and at the end of each test. The protocol is based on color categories of possible fungal growth which can be observed or ascertained on each individual wood chip or substrate with the unaided eye at normal reading distance. When the substrate is sterilized, only one color category, that of the invention candidate, will be recognized and the protocol involves simple visual inspection of all wood chips to determine the number or percentage of chips which show visible growth of candidate fungus. When the growth evaluation is carried out on non-sterile substrates, different color categories will be usually recognized to distinguish between the invention or inoculated fungus and those which naturally infested the substrate. The inoculated candidate, typically the lightest color, will be identified and the number or percentage of wood chips visibly exhibiting such growth will be counted. Results reported below are given in terms of the percentage of the wood chips observed to exhibit growth of our desired fungus in each test case. Treated, non-sterile wood chips may show growth in other areas of the chips of other organisms, such as a black coloring fungi, and such background growth coloring may be separately recorded in a similar fashion. Such background growth should not be taken as negating otherwise positive growth results with the inoculated fungus; but the more desired fungal candidates are clearly those which best suppress or dominate over such background growth.

In the following Examples two different isolates of *Phlebia Tremellosa* are evaluated under the identifications BRI-94 and BRI-118.

EXAMPLE 1

Growth and Removal of Pitch on Sterile Southern Yellow Pine:

An evaluation of fungal growth of BRI-118 on Southern Yellow Pine was performed on sterile wood chip samples. The samples had been aged about 2 days after chipping, and had about 5% background growth at the time of sterilization. Each of the samples contained 500 grams of wood chips, prepared as described above. An inoculant was prepared as described above, and 25 grams of homogenized mycelial mat slurry (wet weight) were used to inoculate sample lots of the 500 grams of chips in the manner described above, representing a dosage of $1.4 \times 10^7$ CFU/500 g. of chips. The bags were then stored at room temperature for a total period of 14 days. Evaluation of the growth of the fungus was performed at the third, sixth and fourteenth day after the inoculation of the samples. The results of this growth on sterile southern pine are reported in Table 1 below, which average three replications. Pitch reduction is reported in Table 2 against a water inoculated control.

TABLE 1

Growth on Sterile Southern Yellow Pine

| Isolate | 3 days growth | 6 days growth | 14 days growth |
|---|---|---|---|
| BRI-118 | 5% | 100% | 100% |

TABLE 2

Pitch Reduction on Sterile Southern Yellow Pine

| Isolate | % DCM | % Reduction |
|---|---|---|
| Control | 4.70 | — |
| BRI-118 | 3.37 | 28.3 |

EXAMPLE 2

Example 1 is repeated except that: 1) both BRI-94 and BRI-118 are evaluated; and 2) the Southern Yellow Pine wood chips were sterilized 2 days after chipping and had at the time of sterilization 15% background growth which together with other information suggested that the wood was well aged before chipping and the wood chips would be difficult hosts for fungal growth and/or pitch degradation. Growth results are reported in Table 3 and pitch reduction in Table 4.

TABLE 3

Growth On Sterile Southern Yellow Pine

| Isolate | 6 days growth | 9 days growth | 14 days growth |
|---|---|---|---|
| BRI-94 | 10% | 100% | 100% |
| BRI-118 | 10% | 10% | 20% |

TABLE 4

Pitch Reduction On Sterile Southern Yellow Pine

| Isolate | % DCM | % Reduction |
|---|---|---|
| Control | 2.44 | — |
| BRI-94 | 1.76 | 27.9% |
| BRI-118 | 1.89 | 22.5% |

EXAMPLE 3

Removal of Pitch in Non-Sterile Softwood (Pine)

The two different isolates of the fungus *Phlebia tremellosa* designated BRI-94 and BRI-118 were evaluated for their efficacy in the removal of pitch in non-sterile Southern Yellow Pine and other characteristics. Control samples were also evaluated to provide a comparative indication. Control samples included a non-inoculated control sample which was maintained frozen (−200° C.) throughout the period of the test, and a water inoculated ambient control sample which was maintained at room temperature. The ambient temperature control was used as an indicator of the effect on pitch reduction of background organisms present on the non-sterile wood chip samples, and pitch removal of the fungal isolates was measured as a percent reduction below that of the ambient control. All evaluations were performed on 500 gram samples of non-sterile Southern Yellow Pine wood chip samples after 14 days of growth after inoculation, with each test run in triplicate and the results averaged. The wood chips were of unknown age, but had at time of inoculation 20% blue stain and 2% Yellow stain background growth, again suggesting an aged wood source and substrates which are difficult challenges for pitch removal. For comparison, the tests also involved the fungal species *Ophiostoma piliferum* in the form of the product available under the registered trademark CARTAPIP® 97 which normally performs very well on non-sterile Southern Yellow Pine.

Each of the samples were evaluated for the amount of DCM extractable in accordance with the protocol described TAPPI Procedure T204 OS-76. Analysis of the Klason lignin was performed upon selected wood chip samples to provide an indicator of the degradation of lignin in the sample chips; quantitative determination of five principal monosaccharides (glucan, mannan, arabinan, xylan and galactan) was performed on an absolute basis so to define the carbohydrate composition of the wood. This Klason lignin analysis was performed generally in accordance with the testing protocol of TAPPI T249 cm-85 "Carbohydrate composition of extractive-free wood and good pulp by gas-liquid chromatography" (1984; TAPPI). In summary, Klason lignin analysis according to the TAPPI T249 cm-85 protocol is as follows; samples are hydrolyzed with sulfuric acid using a two-step technique; a portion of the hydrolyzate is then neutralized and the sugars present in the sample reduced with sodium borohydrate to the alditols, which are then acetylated with acetic anhydride and pyridine, and the alditol acetates then dissolved in methylene chloride and then used for injection into the gas chromatograph. Further, for selected wood chip samples an analysis of the carbohydrates was performed so as to evaluate the extent of cellulose and hemicellulose degradation.

In this Example, the inoculum involved 15 grams of mycelial mat (wet weight) representing a CFU count of $2.3 \times 10^6$/g. of homogenized mycelial mat in the case of BRI-94 and a CFU count of $3.5 \times 10^6$/g. of homogenized mat in the case of BRI-118.

Results of the samples being evaluated, % DCM extractives and % Klason lignin are reported on Table 5, and the carbohydrate analysis of selected samples are reported on Table 6, both below.

TABLE 5

% DCM extractives and % Klason lignin

| Fungus | % DCM extractives | % Pitch Reduction Over Ambient Control | % Klason lign |
|---|---|---|---|
| non-inoculated, Frozen control | 2.66 | — | 29.4% |
| non-inoculated, ambient control | 2.35 | — | 29.6% |
| CARTAPIP$^R$97[a] | 2.11 | 10.2% | — |
| BRI-94 | 1.32 | 44% | — |
| BRI-118 | 1.52 | 35.3% | 29.5% |

[a] Dose of $5 \times 10^8$ CFU per 500 g. of chips represents colony forming Units based solely on spore count for *O. piliferum* (product only contains spores).

TABLE 6

Carbohydrate Analysis For BRI-118 Chips

| Sample: | arabinan | xylan | mannan | galactan | glucan |
|---|---|---|---|---|---|
| ambient control | 1.07 | 5.6 | 11.5 | 2.4 | 40.5 |

TABLE 6-continued

Carbohydrate Analysis For BRI-118 Chips

| Sample: | arabinan | xylan | mannan | galactan | glucan |
|---|---|---|---|---|---|
| BRI-118 | 1.06 | 5.6 | 11.3 | 2.5 | 39.5 |

As may be seen from the Klason lignin test results, the fungus of the invention were found not to appreciatively effect the lignin content of the wood chip samples. Surprisingly, the fungal species of the invention caused a significant reduction in the pitch content of the samples, it being noted that CARTAPIP®97 is regarded as a potent degrader of pitch.

As may be seen from the results of Table 6, there was not an appreciable loss in the amount of carbohydrates in samples of pine wood chips which were treated with our fungus as compared to the ambient control sample. Hence no reduction of cellulose and/or hemicellulose was indicated as a result of the pitch reducing treatments.

In growth experiments conducted in connection with this Example 3, it was difficult to detect growth of the fungi even after 12 days with CARTAPIP®97 showing virtually no easily detectable growth, BRI-94 showing only 20% and BRI-118 only 10%. Various possible explanations for this phenomenon include aged condition of the chips, the tendency of these fungi to grow colorless and/or penetration and internal action by the fungi.

EXAMPLE 4

Growth and Pitch Reduction on Non-Sterile Hardwoods

Following the procedure of the preceding Examples, BRI-118 was evaluated for growth and pitch reduction on 500 g. samples of non-sterile mixed hardwood wood chips which were inoculated one day after chipping and which showed no background growth at time of inoculation. The hardwood mixture involved 75% maple, 20% yellow birch and 5% oak. The BRI-118 was harvested from an 8 day shaking flash culture and each inoculum involved 3 g. of mycelial mat with an estimate CFU count of $7.1 \times 10^5$/g. of mat. Treatment time was 14 days. Growth results are reported in Table 7 and pitch reduction in Table 8 (against the ambient control).

TABLE 7

Growth of BRI-118 on non-sterile Mixed Hardwoods

| Isolate | 3 days growth | 14 days growth |
|---|---|---|
| BRI-118 | 50% | 90% |

TABLE 8

Pitch Reduction By BRI-118 on Non-Sterile Mixed Hardwoods

| Isolate | % Ethanol/Toluene Extractives | % Reduction Over Ambient Control |
|---|---|---|
| Frozen Control | 4.12 | — |
| Ambient Control | 3.55 | — |
| BRI-118 | 2.73 | 23.0% |
| CARTAPIP$^R$97 | 2.92 | 17.7% |

Table 7 indicates good detectable growth of the fungus of the invention on hardwoods and Table 8 indicates a superior pitch reduction for our fungus over CARTAPIP®97.

EXAMPLE A

GROWTH CHARACTER OR FUNGI IN LIQUID SHAKE FLASK CULTURE

Phlebia Tremellosa (BRI-118) was grown in shake flask liquid culture using 500 ml. of a YNPD medium prepared as above described (EXPERIMENTAL). The medium was inoculated with a small plug of mycelia from an actively growing malt/yeast extract agar plate. The flask was shaken at 200 rpm at 23°–25° C. for 11 days and a 1 ml sterile sample from each culture was removed for microscopic analysis. The culture showed a dense growth of mycelial balls and the culture masses were also indicated to include from about 0.5 to 1.5% blastospores. This product can be used as inoculum or processed in various ways to produce inoculum forms, e.g. by homogenizing and freezing for later use. Inoculum based essentially on the spore content of the cultures may also be prepared by freeze drying.

What is claimed is:

1. A process for reducing the pitch content of pulpwood or of a pulp comprising applying to the pulpwood or pulp an inoculum of a species of the fungus *Phlebia tremellosa* which is capable of reducing pitch, the inoculation being in an amount sufficient upon fungal growth from the inoculation to reduce the pitch content of the pulpwood or pulp, and maintaining the inoculated pulpwood or pulp under conditions which allow fungal growth from the inoculation for a time sufficient to effect a reduction of the pitch content of the pulpwood or pulp by such inoculated fungal growth.

2. The process according to claim 1 for reducing the pitch content of pulpwood or of a pulp retaining at least 60% by weight of its original lignin content comprising applying to the pulpwood or pulp an inoculum a species of the fungus *Phlebia tremellosa* capable of reducing pitch, the inoculation being in an amount sufficient upon fungal growth from the inoculation to reduce the pitch content of the pulpwood or pulp, and maintaining the inoculated pulpwood or pulp under conditions which allow fungal growth from the inoculation for a time sufficient to effect a reduction of the pitch content of the pulpwood or pulp by such inoculated fungal growth.

3. The process of claim 2 in which unsterilized pulpwood is inoculated to reduce its pitch content.

4. The process of claim 3 in which the unsterilized pulpwood is unsterilized refined pulpwood, in which the inoculated refined pulpwood is accumulated in a mass and in which the accumulated mass is maintained under conditions which allow fungal growth a time sufficient to effect a reduction of the pitch content of the pulpwood by the inoculated fungal growth.

5. The process of claim 4 in which the refined pulpwood is wood chips and the inoculum is applied by spraying of wood chips with the inoculum prior to accumulation of the wood chips in the mass.

6. The process of claim 3 in which the inoculum is obtained from a biologically pure fungal culture.

7. The process of claim 3 in which the fungus has at least the ability to reduce pitch on sterilized Southern Yellow Pine that is possessed by the strain of NRRL Accession No. 21200.

8. The process of claim 2 in which first stage mechanical pulp is treated to reduce its pitch content.

9. The process of claim 3 in which a debarked or undebarked timber or log is treated to reduce its pitch content.

10. The process of claim 2 in which the inoculated pulpwood or pulp is maintained under fungal growth conditions for a period of from 4 to 20 days from inoculation.

11. The process of claim 5 in which the inoculated pulpwood is maintained under fungal growth conditions for a period of from 4 to 20 days from inoculation.

12. The process of claim 7 in which the pulpwood is in the form of wood chips.

13. The process of claim 12 in which the wood chips are Southern Yellow Pine wood chips.

14. The process of claim 5 in which the wood chips are softwood wood chips.

15. The process of claim 5 in which the wood chips are hardwood wood chips.

16. The process of claim 3 in which the fungus has at least the ability to reduce pitch on sterilized Southern Yellow Pine that is possessed by the strain of NRRL Accession No. 21253.

17. The process of claim 3 in which the fungus is the fungus of NRRL Accession No. 21200.

18. The process of claim 3 in which the fungus is the fungus of NRRL Accession No. 21253.

* * * * *